United States Patent [19]

Weber

[11] Patent Number: 5,490,409

[45] Date of Patent: Feb. 13, 1996

[54] ADJUSTABLE CAM ACTION ROD BENDER FOR SURGICAL RODS

[75] Inventor: Helmut Weber, Emmingen, Germany

[73] Assignee: K-Medic, Inc., Northvale, N.J.

[21] Appl. No.: 335,451

[22] Filed: Nov. 7, 1994

[51] Int. Cl.⁶ .................................................... B21D 7/06
[52] U.S. Cl. ........................ 72/458; 72/409.1; 72/216; 72/217; 140/106
[58] Field of Search ........................ 72/458, 215, 217, 72/218, 219, 220, 388, 387, 409, 479; 140/106

[56] References Cited

U.S. PATENT DOCUMENTS

| 537,550 | 4/1895 | Schacht | 72/219 |
|---|---|---|---|
| 1,824,219 | 9/1931 | Loveless | 72/216 |
| 2,986,194 | 5/1961 | Marco | 72/215 |
| 4,474,046 | 10/1984 | Cook | 72/409 |

FOREIGN PATENT DOCUMENTS

| 1424910 | 9/1988 | U.S.S.R. | 72/218 |
|---|---|---|---|

OTHER PUBLICATIONS

French Rod Bender, KM 46–664. K Medic Surgical Instruments 117 Fort Lee Road, Leonia, NJ 07601

Primary Examiner—David Jones
Attorney, Agent, or Firm—Alfred Walker

[57] ABSTRACT

A cam action surgical rod bender includes a locking assembly which locks a bending knob in place. The rod bender includes a knee lever configuration for keeping the bending knob still, wherein a pin is moved downwardly along a channelled cam surface to provide stability when locking the bending knob in place against the round support plate at the hinge portion of the rod bender.

5 Claims, 6 Drawing Sheets

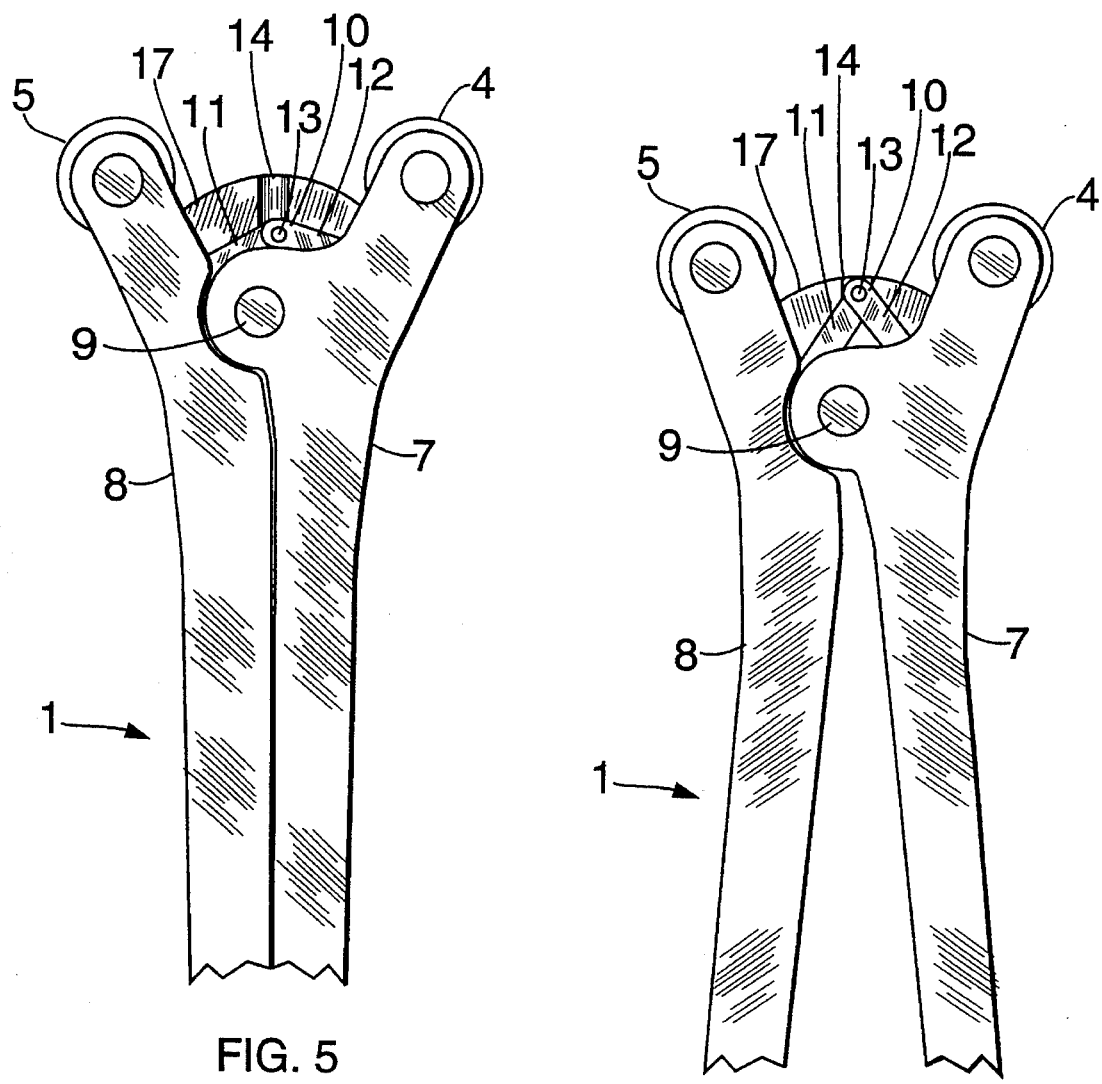
FIG. 5
FIG. 6
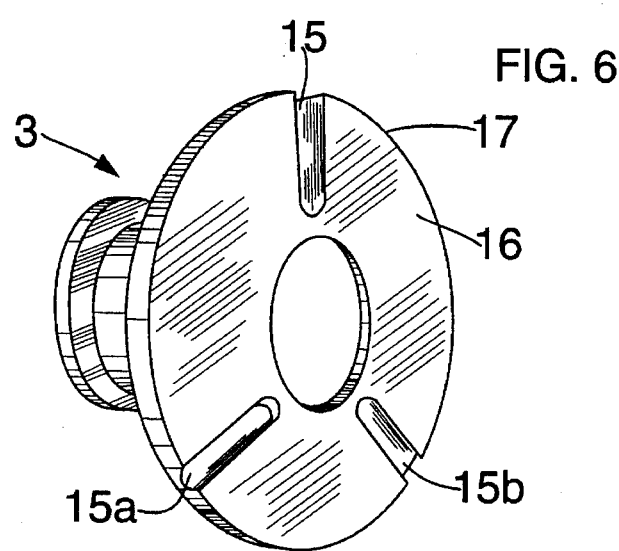
FIG. 7

1

ADJUSTABLE CAM ACTION ROD BENDER FOR SURGICAL RODS

BACKGROUND OF THE INVENTION

This invention relates to a cam action, adjustable rod bender for surgical rods, more specifically, to a rod bender with a rotatable eccentric bending knob which rotates to one of a plurality of radius bend positions of use for insertion of a surgical rod between the rotatable knob and two fulcrums at the tops of each of the two handles, against which the rod is bent. When not in use, the cam rotates to alternate positions of radius bends.

Various attempts have been made to provide a rod bender for surgical rods, such as the French Rod Bender model no. KM 46-664 of the assignee K Medic, Inc. of Leonia, N.J. 07605 of the Applicant herein. While the prior art rod benders perform the same function of bending surgical rods about a circumferential recess of the knob, they have a fixed center cam which only allows the rod to be bent to a single radius. In contrast, the present rod bender includes an adjustable cam with three positions for three different radius bends.

The prior art does not disclose a cam action, rotatable movement of a movable bending knob for bending surgical rods into one of three desired radius bends by means of a locking cam bending knob, which knob is also retractable, outward away from a hinge about which two handles rotate, so that the knob can be rotated to one of a plurality of positions, such as three positions. In order to bend different sized rods, a separate device known as a reduction ring must be placed over the center knob of instrument. The disadvantages of the reduction ring are: 1) it is not part of the instrument and can become separated and lost 2) it is difficult to use 3) it can be hard to remove after use.

In contrast, the present invention provides a unique knee lever configuration which keeps the bending knob still while both handles are moved. The knee lever configuration includes two movable arms joined at a pinned joint, wherein a pin is slightly movable within a channel of a plurality of channels on a rear face of a round plate against which the bending knob is rotatably moveable to one of three desired positions. The pin slides within each channel, when the direction of the bending knob rotates 120 degrees to a desired locking position, against the round plate.

The knob is retracted outward, which outward movement is limited by an internal coil spring normally holding the knob in place against the round support plate.

Furthermore, for convenience another feature of the bending knob is found in that the bending knob includes equally spaced radius indentations to provide a good grip for the surgeon's hand while indexing.

Previous attempts to provide a surgical rod bender have provided an unadjustable assembly wherein a bending knob is provided at the hinge of two outwardly movable handles, which handles are each provided with bending surfaces. The rod is conditionally bent between the bending knob and the two bending surfaces. This unadjustable feature is undesirable, since it cannot adjust to varying radius bends, resulting in restrictions in the bending configuration of the surgical rods.

Furthermore, the prior art surgical rod bender do not describe an adjustable smooth cam acting rod bender with a locking bending knob which moves in a rotatable manner around a cam follower plate as the present invention provides.

2

The present invention improves upon the prior art by providing not only a cam action surgical rod bender assembly, but also a locking assembly which locks the knob in place when not in use. The present invention provides stability by the knee lever configuration for keeping the bending knob still, wherein a pin is moved downwardly along a channelled cam surface to provide stability when locking the bending knob in place against the round support plate at the hinge portion of the rod bender assembly.

OBJECTS OF THE INVENTION

It is therefore an object of the invention to provide an adjustable cam action surgical rod bender assembly for bending surgical rods to a desired radius of curvature.

It is a further object to provide a rotatable locking bending knob which can be locked in place when in use and the desired position for bending surgical rods.

It is a further object to provide a stable, twist lock cam acting bending knob for rod benders that firmly locks the adjustable bending knob in place.

It is a further object to provide for a simple mounting of the adjustable bending knob assembly to the hinge portion of the rod bender handles.

It is a further object to provide a rod bender assembly which has structural strength and integrity.

It is a further object to provide a bending knob which rotates to a plurality of desired positions within a surgical rod bender tool, so that a variety of radius bend curvatures may be obtained.

It is yet another object to provide a bending knob which is spring loaded, so that it can be retracted outward for adjustment to the desired radius bend curvature position.

It is a further object to provide a unique knee lever configuration to keep the bending knob still while the handles at the rod bender are moved during use.

It is yet another object to provide an index handle for a bending knob which is easily gripped.

It is yet another object to provide an adjustable surgical rod bender which improves over the disadvantages of the prior art.

It is another object to provide a rod bender which bends any size rod, up to 7 mm in diameter, to three different angles.

It is yet another object to provide a rod bender which eliminates the need for a reduction ring used on prior art rod benders.

SUMMARY OF THE INVENTION

In furtherance of the aforesaid objects, the present invention provides a new and useful surgical rod bender incorporating a new "cam action bending knob" that firmly locks in place in one of three radius bend positions. The cam action bending knob assembly allows for alternative surgical rod curvatures. The present invention is designed for use by surgeons who bend rods to fit within the body, to stabilize fractured bones, vertebrae, etc. It includes a retractable feature that allows the bending knob to rotate to desired positions of use.

The present invention is designed for simple operation by a surgeon, who bends surgical rods by moving handles together during the bending process.

The present invention provides a safe, convenient mechanism to secure the rod in place for bending to a desired radius of curvature. The present rod benders are non-adjustable and therefore limited in use. The present invention solves this adjustability problem, and, when in use, the bending knob is held still while the handles are spread apart in the bending process.

The bending knobs assembly locks in place, is of an advanced design and includes the following features and benefits:

The preassembled unit construction permits direct rod bending during surgery. The configuration is ambidextrous, that is, it can be used, on either the left or right side, with the rugged design using two spreadable operating handles.

The present invention tightly holds a knob in place in and an embedded compression spring returns the retractable bending knob to a position of use after adjustment for the desired radius bend of curvature.

The preferred embodiment provides a support plate to support the bending knob, which support plate is intended to accommodate the pin of the knee lever. The support plate supports the twist lock bending knob, which bending knob secures the surgical rod in place against two bending surfaces at the end of each handle, which handles are hingeably attached to permit outward movement during the bending process.

The bending knob is secured to an axial shaft, which shaft is disposed to the coil spring to hold the retractable bending knob in place. A first cam follower pin of the knee lever slides along channelled cam surfaces within the support plate. The movable bending knob rotates to the desired position of use.

BRIEF DESCRIPTION OF THE DRAWINGS

The present invention can best be understood in light of the attached drawings in which:

FIG. 5 is a closeup rear elevational view of the rod bender when the handles are closed.

FIG. 6 is a closeup rear elevational view of the rod bender as in FIG. 5, showing the knee lever portion and the handles in a partially opened position.

FIG. 7 is a perspective view of the support plate portion of the rod bender as in FIG. 3.

DETAILED DESCRIPTION OF THE DRAWINGS

Figure 1:
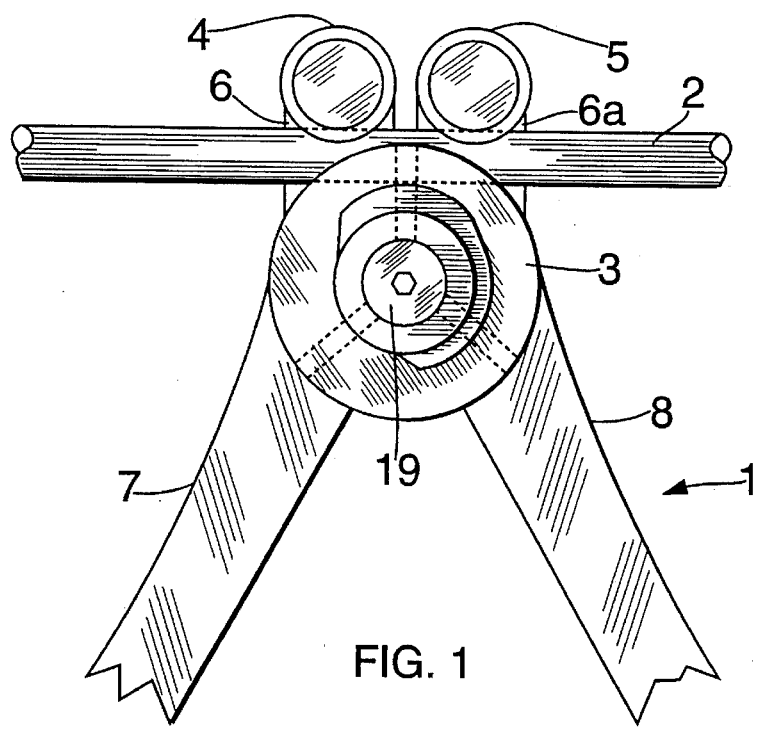
FIG. 1 is a closeup front elevational view of the bending portion of the rod bender, showing a surgical rod in an unbent position.
Figure 2:
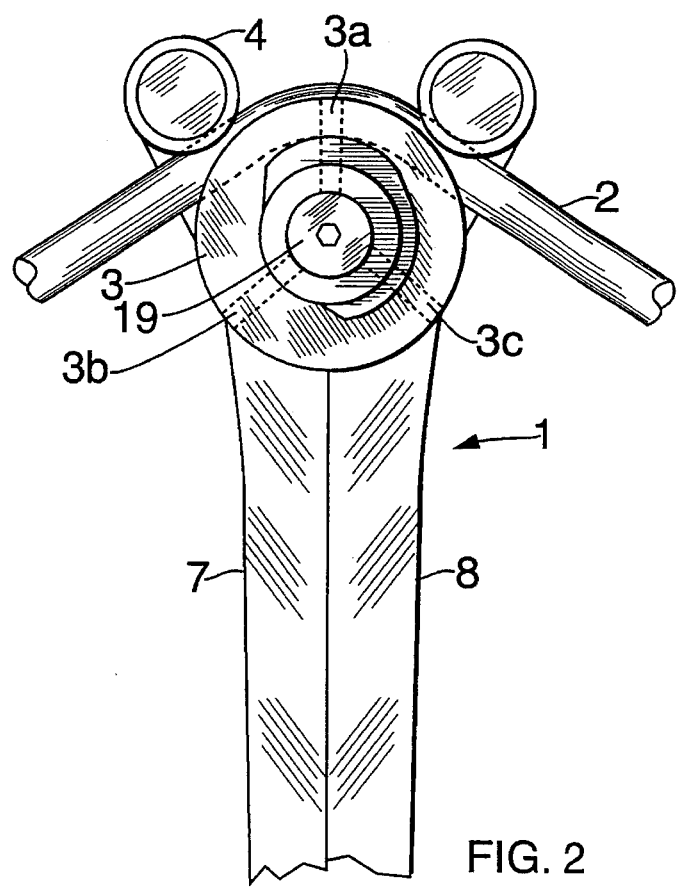
FIG. 2 is a closeup front elevational view of the bender as in FIG. 1, showing a surgical rod in cam bent position.
Figure 3:
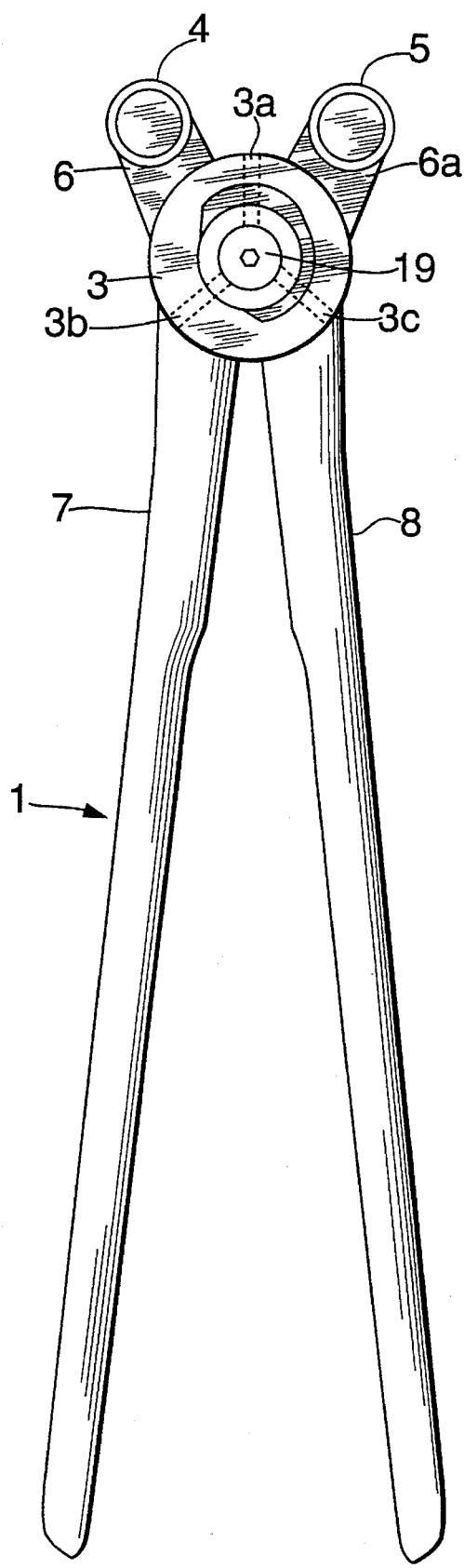
FIG. 3 is a front elevational view of the rod bender.
Figure 4:
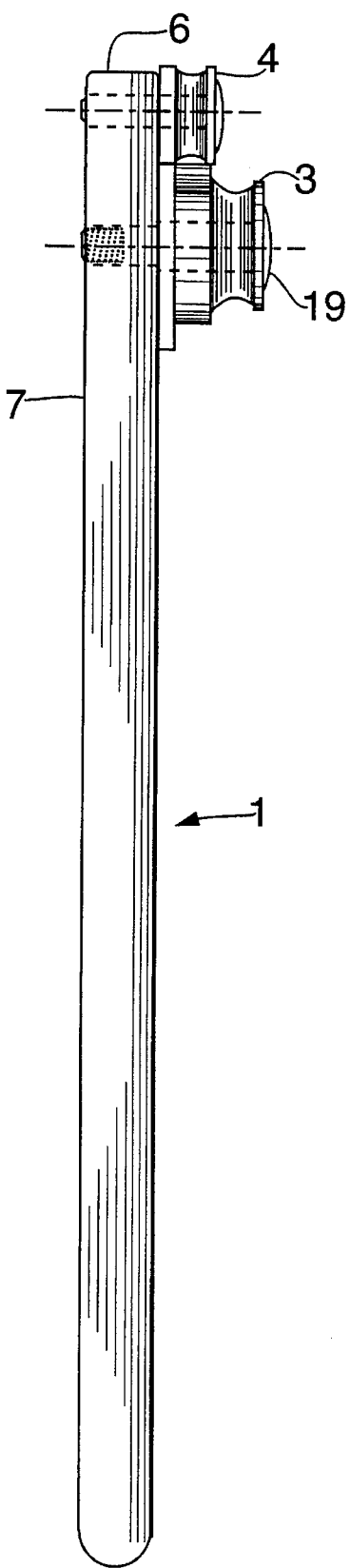
FIG. 4 is a left side elevational view of the rod bender as in FIG. 3.
Figure 8:
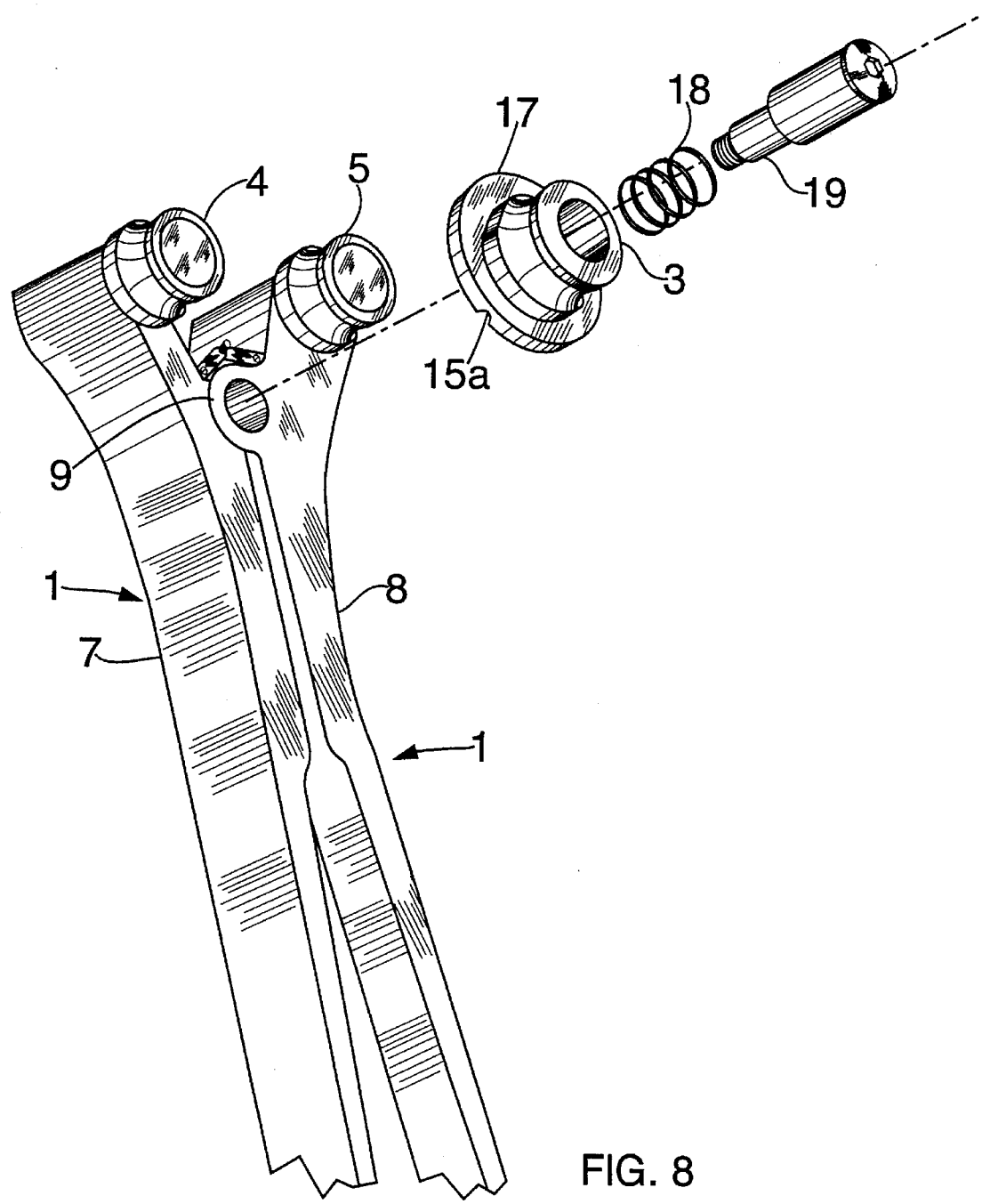
FIG. 8 is an exploded closeup perspective view of the rod bender as in FIG. 3.
Figure 9:
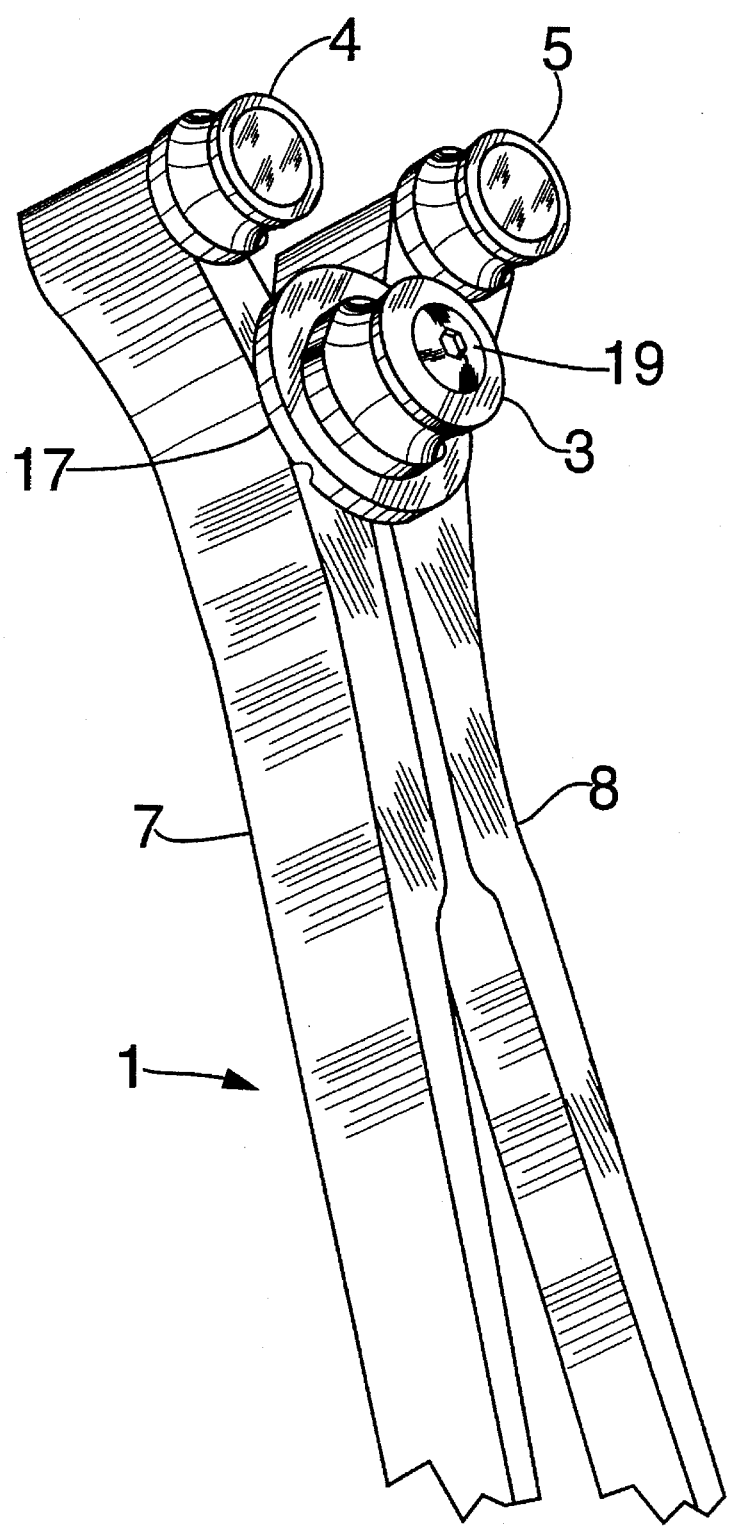
FIG. 9 is a close up perspective view of the rod bender as in FIG. 3.

As shown in FIGS. 1–9, the present invention includes a cam action, adjustable rod bender 1 for surgical rods 2, with a rotatable eccentric bending knob 3 which rotates around a pivot 9 to one of a plurality of radius bend positions 3a, 3b, 3c of use for insertion of a surgical rod 2 between the rotatable knob 3 and two fulcrums 4, 5 at the tops 6, 6a of each of the two handles 7, 8, against which the rod 2 is bent. When not in use, the cam rotates to alternate positions of radius bends.

Figure 10:
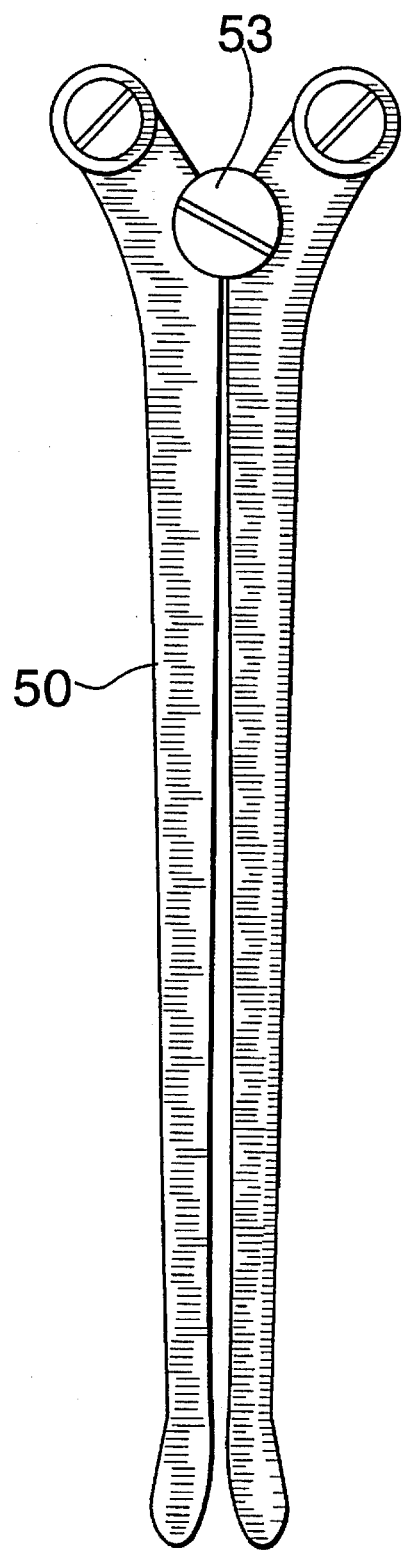
FIG. 10 is a front elevational view of a prior art rod bender.

FIG. 10 describes a prior art rod bender 50 for surgical rods, such as the French Rod Bender model no. KM 46-664 of the assignee K Medic, Inc. of Leonia, N.J. 07605 of the Applicant herein. The prior art rod benders 50 perform the same function of bending surgical rods about a circumferential recess of a non-rotatable knob 53. They have a fixed center cam which only allows the rod to be bent a single radius.

In contrast, the present rod bender 1 includes an adjustable cam with three positions 3a, 3b, 3c for three different radius bends.

In the present invention knob 3 is also retractable, outward away from a hinge 9 about which two handles 7, 8 rotate, to enable the knob 3 to rotate to one of three positions 3a, 3b, 3c.

Rod bender 1 also provides a unique knee lever 10 to maintain bending knob 3 still while handles 7, 8 are moved. Knee lever 10 includes two movable arms 11, 12 joined at a pinned joint 13, wherein a pin 14 is slightly movable within a channel 15 of a plurality of channels 15, 15a, 15b on a rear face 16 of round plate 17 against which plate 17 the bending knob 3 is rotatably moveable to one of three desired positions 3a, 3b, 3c. Pin 14 slides within each channel 15, when the direction of the bending knob 3 rotates 120 degrees to a desired locking position, against round plate 17.

Knob 3 is retracted outward, and its movement is limited by an internal coil spring 18 which holds knob 3 in place against round support plate 17.

Bending knob 3 includes equally spaced radius bends to provide a good grip for the surgeon's hand while indexing.

Rod bender 1 is an adjustable smooth cam acting rod bender with locking bending knob 3 which moves in a rotatable manner around a cam follower plate 17.

Rod bender 1 is stable because knee lever 10 keeps bending knob 3 still, wherein pin 14 moves downwardly along channelled cam surface 15 to provide stability when locking bending knob 3 in place against round support plate 17 at the pivot 9 portion of rod bender 1.

The cam action bending knob 3 allows for alternative surgical rod curvatures. Therefore, surgeons can bend rods 2 to custom fit within the body, to stabilize fractured bones, vertebrae, etc.

Bending knob 3 rotates about an axial shaft 19, which shaft 19 is disposed to coil spring 18 to hold the retractable bending knob 3 in place.

Other modifications may be made to the present invention without departing from the scope of the invention.

I claim:

1. A cam action, adjustable rod bender for bending a surgical rod, comprising two handles bendable about a pivot, said pivot having a rotatable eccentric bending knob mounted on said pivot, said bending knob rotatable to one of a plurality of selected radius bend positions of use, for insertion and bending of a surgical rod within a recess between said rotatable bending knob and a pair of fulcrums, each fulcrum located at a top portion of each of said handles, the rod being bendable by contact of each of said fulcrums against the rod, said fulcrums contacting the rod within said recess against said bending knob, said bending knob rotatable to a plurality of alternate selectable positions of radius bend, said rod bender further including a knee lever, said knee lever holding said bending knob still while said handles are moved, said knee lever including two movable arms joined at a further pivot by a pin, said pin slidably movable within a selected channel of a plurality of channels located on a rear face of a plate, said plate positioned between said two handles and said bending knob against which said plate said bending knob is rotatably movable, to one of said alternate positions of radius bend, said pin slidably movable within each said channel, said bending knob rotatable to a desired locking position against said round plate.

2. The rod bender as in claim 1 further comprising said bending knob being retractable outward away from said pivot, about which said pivot each said two handles rotate.

3. The rod bender as in claim 2 wherein said bending knob is retractable outward, which outward movement is limited by an internal coil spring holding said bending knob in place against said support plate.

4. The rod bender as in claim 1 wherein said bending knob includes a plurality of equally spaced radius gripping indentations.

5. An instrument for bending a rod comprising:

a pair of pivotable engaged oppositng handles, a pivot interconnecting said handles so as to be pivotable thereabout, said pivot substantially dividing said arms into a handle portion for opening and closing said arms and a bending portion operable by said handle portion;

a bending means mounted on said bending portion, said bending means including a bending knob mounted on said pivot, said bending knob having a plurality of selectively lockable bending surfaces circumferentially spaced around a peripheral edge of said bending knob for bending a portion of the rod, and a pair of fulcrums, each said fulcrum located on each of said handles, and pivotable therewith, said bending knob being positioned with respect to said pair of fulcrums so as to define a recess therebetween for insertion of the rod therein when said handles are in an open position, said fulcrums bending the rod about said bending knob when said handles are rotated about said pivot point to a desired closed position, and, said rod bender further including a knee lever, said knee lever holding said bending knobs still while said handles are moved to a closed position, said knee lever including two movable arms joined at a further pivot by a pin, said pin slidably movable within a selected channel of a plurality of channels located on a rear face of a plate, said plate positioned between said two handles and said bending knob, against which said plate said bending knob is rotatably movable, to one of said alternate positions of a radius bend, said pin slidably movable within each said channel, said bending knob rotatable to a desired locking position against said round plate.

* * * * *